United States Patent [19]

Namikawa et al.

[11] Patent Number: 5,633,426
[45] Date of Patent: May 27, 1997

[54] IN VIVO USE OF HUMAN BONE MARROW FOR INVESTIGATION AND PRODUCTION

[75] Inventors: Reiko Namikawa, Palo Alto, Calif.; Seishi Kyoizumi, Hiroshima, Japan; Joseph M. McCune, San Francisco; Hideto Kaneshima, Palo Alto, both of Calif.

[73] Assignee: Systemix, Inc., Palo Alto, Calif.

[21] Appl. No.: 194,717

[22] Filed: Feb. 10, 1994

Related U.S. Application Data

[63] Continuation-in-part of Ser. No. 904,886, Jun. 25, 1992, abandoned, and Ser. No. 90,571, Jul. 12, 1993, abandoned, which is a continuation of Ser. No. 599,649, Oct. 18, 1990, abandoned, said Ser. No. 904,886, is a continuation of Ser. No. 529,217, May 25, 1990, abandoned.

[51] Int. Cl.$^6$ .......................... A61K 49/00; A61K 48/00
[52] U.S. Cl. .................. 800/2; 424/9.2; 424/93.7; 424/549; 424/577; 424/578; 424/580; 424/582; 424/579; 800/DIG. 5; 623/11
[58] Field of Search ....................... 800/2, DIG. 5; 623/11; 424/9, 549, 577, 578, 580, 582, 579, 93.7, 9.2

[56] References Cited

PUBLICATIONS

Mosier et al., Nature 335: 256–259 (1988).

McCune et al., Science 241: 1632–1639 (1988).

Kamel-Reid et al., Science 242: 1706–1709 (1988).

Groscurth et al., Anat. Embryol. 165: 291–302 (1982).

Tach et al., Diabetes 33: 1180–1187 (1984).

Bastert et al., Endo. 101(2): 365–368 (1977).

*Primary Examiner*—Jasemine C. Chambers
*Attorney, Agent, or Firm*—Pamela J. Sherwood; Fish & Richardson P.C.

[57] ABSTRACT

Chimeric immunocompromised hosts are provided, comprising human bone marrow of at least 4 weeks from the time of implantation. The bone marrow is found to assume the normal population of bone marrow except for erythrocytes. The bone marrow may be used to study the effect of various agents on the proliferation and differentiation of hematopoietic cells.

20 Claims, No Drawings

IN VIVO USE OF HUMAN BONE MARROW FOR INVESTIGATION AND PRODUCTION

CROSS-REFERENCE TO RELATED APPLICATIONS

This application is a continuation-in-part of application Ser. No. 07/904,886, filed Jun. 25, 1992, now abandoned, which is a continuation of application Ser. No. 07/529,217, filed May 25, 1990 now abandoned. This application is a continuation-in-part of application Ser. No. 08/090,571, filed Jul. 12, 1993, now abandoned, which is a continuation of application Ser. No. 07/599,649, flied Oct. 18, 1990 now abandoned.

INTRODUCTION

1. Technical Field

The field of this invention is the use of human bone marrow for investigational purposes and production of hematopoietic cells and hematopoietic growth factors.

2. Background

The mammalian blood system is an extraordinarily complex system, where it is believed that all of the varied blood cells emanate from a single progenitor cell, referred to as the hematopoietic stem cell. Present theory supports the notion that there is a single cell which is self-renewable and, under the stimulus of various factors, is able to differentiate and mature, becoming dedicated to the formation of cells of the numerous compartments of the hematopoietic system. The hematopoietic stem cell is known to reside in bone marrow, although it would appear that there may be privileged sites in the bone marrow where the stem cell resides.

An understanding of the manner in which blood cells are formed and maintained is essential to many areas of medicine. Many diseases are associated with the inability of the blood cells to respond to various stresses, such as pathogen invasions, injection of toxic substances, neoplastic conditions, irradiation, and the like. In order to be able to understand how the blood cells respond to these various stresses, it is necessary to study bone marrow and the peripheral blood in vivo. While animal models provide some insight into the nature of the hematopoietic system and the mechanism for the response of the hematopoietic system to various stimuli, there are still significant differences between the nature and response of various laboratory animals and human hematopoietic cells.

Recently, chimeric mice were developed, where human fetal tissue was introduced into CB-17 scid/scid mice to provide the chimeric SCID-hu mouse. The mice were shown to maintain for extended periods of time, human fetal lymph node and thymus and provide for peripheral blood cells, when supplied with a source of hematopoietic stem cells from fetal liver. While in some instances, the maintenance of human peripheral blood cells could be extended for long periods of time, in all instances the human cells were only a very small proportion of the total number of peripheral blood cells, frequently substantially fewer than one percent.

In many instances, it would be desirable to have a relatively high proportion of the peripheral blood cells as human cells and desirably have a significant proportion of the total number of hematopoietic cells being human cells, particularly with circulating myelomonocytic cells and red blood cells besides lymphoid cells. Such a system would allow the opportunity for immunization to obtain a strong immune response from the human cells, studies of various diseases and their effect on the various hematopoietic cells and studies of drugs against various diseases and their effect on the hematopoietic cells.

There is, therefore, substantial interest in developing systems which allow for long-term maintenance of human hematopoietic cells in an in vivo environment, where the cells may be studied and provide for a reasonably reliable prognosticator of the response of the cells in a human host.

RELEVANT LITERATURE

References concerned with immunoincompetent hosts, particularly CID, or SCID hosts include McGuire et al., *Clin. Immunol. and Immunopath.* (1975) 3:555–566; Perryman and Torbeck, *J. Am. Vet. Med. Assoc.* (1980) 176:1250–1251; Shultz and Sidman, Genetically-determined Murine Models of Immunodeficiency, The Jackson Laboratory, Bar Harbor, Me.; Bosma et al., *Nature* (1983) 301:527–530; Custer et al., *Amer. J. Path.* (1985) 120:464–477; Dorshkind et al., *J. of Immunol.* (1985) 134:3798–3801; Keightley et al., *Lancet*, Nov. 1, 1975, 850–853; Touraine, *Immunological Rev.* (1983) 71:103–121; and Fulop and Phillyes, *J. of Immunol.* (1986) 136:4438–4443.

References concerned with xenogeneic cells growing within live hosts include Krueger et al., *J. Inv. Dermatol.* (1975) 64:307–312; Krueger et al., *Proc. Natl. Acad. Sci. USA* (1983) 80:1650–1654; Krueger and Shelby, *J. Inv. Dermatol.* (1981) 76:506–510; Ware et al., *J. Immunol. Meth.* (1985) 85:353–361; Ford et al., *Nature* (1956) 177:452–454; Povlsen et al., *Nature* (1974) 248:247–249; Mannhardt et al., *Thymus* (1982) 4:209–220; Schulte-Wisserman et al., *Scand. J. Immunol.* (1978) 8:387–396; McCune et al., *Science* (1988) 241:1632–1639; Yancopoulos and Alt, Ibid (1988) 241:1581–1583, and references cited therein; Louwagie and Verwilghen, *Nature* (1970) 225:383; Kamel-Reid and Dick, *Science* (1988) 242:1706–1709; and Barr et al., *Science* (1975) 190:284.

See also copending application Ser. No. 287,075, filed Dec. 20, 1987, and EPO 88.312222.8, which are incorporated herein by reference.

SUMMARY OF THE INVENTION

Long-term human bone marrow function is maintained in vivo in immunocompromised mammalian hosts other than primate. Bone marrow slices or fragments, particularly fetal bone marrow, is introduced into the xenogeneic host at a site where vascularization occurs and sufficient time permitted for regeneration of the bone marrow to a population reasonably approximating the original bone marrow population. The long-term bone marrow may be used for investigating the effects of agents on bone marrow function, investigating neoplastic lymphoid tissue in a natural environment, producing specific cell types and investigating various hematopoietic disorders and agents for treating the disorders.

The xenogeneic bone marrow may be introduced into a host depleted of endogenous bone marrow to provide for increased numbers of circulating xenogeneic blood cells. The bone marrow may be present as bone tissue or dispersed bone marrow implanted at a suitable site, or injected into the long bone of the host.

DESCRIPTION OF THE SPECIFIC EMBODIMENTS

Methods and chimeric animals are provided comprising human bone marrow in a xenogeneic host, where the bone marrow finds use for the production of hematopoietic cells, including hematopoietic stem cells, dedicated progenitor cells, mature cells, and stromal cells which support hematopoietic cells, for investigating the effect of agents, both chemical and physical, on the hematopoietic cells and population distribution, and for investigating diseased states in a bone marrow environment, including such diseased states as neoplasia.

The human bone marrow is introduced into the xenogeneic host with the appropriate stroma at a site which permits vascularization of the bone marrow. The bone marrow may then be maintained for extended periods of time, usually at least four weeks, preferably at least six weeks and may be maintained for sixteen weeks or more. It is observed that there is an initial early crisis followed by recovery of hematopoiesis. At weeks two to three, histological examination shows necrosis and/or fibrous changes in the marrow. No clear foci of hematopoietic cells is found on histology sections, although bone elements including osteoblasts are maintained. However, after about four weeks, active hematopoiesis is observed at many sites within the engrafted bones and after six to eight weeks, most of the grafts look similar to normal human bone marrow associated with hematopoiesis. A high degree of cellularity is observed. Wright-Giemsa staining of the cells on cytospin preparations show that the cells exhibit typical morphology of lymphoid, myeloid or erythroid cells at different maturational stages.

When human bone marrow is introduced into a host depleted of endogenous bone marrow, the resulting chimera may have human peripheral blood cells present as at least two percent (2%) of the total peripheral blood cells, preferably at least five percent (5%) of the total peripheral blood cells and more preferably at least about fifteen percent (15%). The human bone marrow source may be introduced before and after ablation to enhance the survival rate of the host upon ablation, particularly by irradiation.

The bone marrow may be fetal or adult, preferably fetal. Long bones are employed, such as tibia, femur, humerus or the like. For fetal bones, the fetus will generally be from about twelve to twenty-four, more usually from about fifteen to twenty-four gestational weeks (g.w.). The bone will generally be at least about 0.25 cm in length and may be 2 cm in length or greater, depending upon the size of the host. For a mouse, 1 cm is found to be a convenient size. For adult bones, the bones may extend to 5 cm or more, depending on the size of the host. The bone may be cut along a longitudinal axis, so that the bone cortex as well as intramedullary regions are exposed to allow for vascularization, or crosssectional to provide tubular slices, from about 2 to 10 long for a mouse host. The bone implants may be implanted at a variety of sites, subcutaneously, intraperitoneally, and the like.

The bone marrow may be introduced into any nonprimate host, particularly a domestic or laboratory animal. Animals include mammals such as murine, particularly mouse or rat, ovine, bovine, equine, lagamorpha, feline, porcine or the like.

The bone marrow in xenogeneic hosts is found to produce most but not all of the lineages of the hematopoietic system at normal levels. Particularly, the erythroid lineage occurs in substantially lower numbers than normal bone marrow, but erythroid progenitors appear to be present at normal human bone marrow levels. However, the dedicated progenitors of the lymphoid and myeloid lineages are able to grow and with appropriate ancillary organs are also able to mature. As to the progenitors and mature cells that appear in low numbers and do not significantly mature, where the failure is due to other than the absence of an organ, e.g., the thymus and T-cells, various human growth factors or compounds having equivalent activity may be added to encourage the differentiation and maturation of the progenitor cells of the bone marrow to mature cells. Furthermore, the absence of such intermediate or mature cells in the bone marrow allows one to use the bone marrow as an assay for compounds having activity in stimulating the differentiation and maturity of such cells.

The extended period of time in which bone marrow may be maintained in xenogeneic hosts substantially mimicking naturally occurring bone marrow in a syngeneic host allows for a wide variety of testing of various agents, both chemical and physical, the production of specific cell types, and the investigation of diseases associated with hematopoietic cells, such as neoplasia, e.g., leukemia and lymphoma. The effects of such agents may be determined as to particular cell types, as to relative populations, as to the phenotypic and/or functional status of cells which do mature, as to stimulation or inhibition of stimulation, or the like.

The bone marrow may be used after four weeks, preferably after six weeks, for determining the effect of agents on differentiation, maturation, stimulation, proliferation, formation of particular subsets of hematopoietic cells, or the like. Physical conditions which may be studied include irradiation, particularly high-energy irradiation, temperature extremes, such as hot and cold, hypoxia, stress, barometric variation, e.g., high or low altitude, or the like.

So far as chemical agents are concerned, there is extensive interest in determining the effect of various chemical agents on hematopoiesis and the various properties of the hematopoietic cells. Regardless of the purpose of the drug, there is an interest in determining whether the drug will adversely effect the immune system. Thus, there would be an interest in studying drugs, particularly at various dosages, as to their effect on hematopoiesis and the various aspects of the immune system. To the extent that factors are involved in the maturation or differentiation of hematopoietic cells, which factors are produced by organs other than the stroma of bone marrow, and the host factor is not a substitute for the human factor, these factors may be studied and assayed in the implanted bone marrow. For example, erythropoietin of animals other than human will not suffice in many cases to be a substitute for human erythropoietin. Thus, the bone marrow may be used to study the activity of various erythropoietin compositions, compositions which inhibit the effect of erythropoietin or can act as a substitute for erythropoietin. One may also study other growth factors, including cytokines, particularly interleukins, colony-stimulating factors, and the like. One can also study the effect of pathogens, particularly unicellular microorganisms and viruses, on the hematopoietic system, using intact pathogens or various components of the pathogens, such as toxins, cell wall fragments, polysaccharides, and the like.

For studying neoplasia, one may introduce various neoplastic cells into the bone marrow and allow the neoplastic cells to grow. Normally, neoplastic cells would be introduced either during or after bone marrow recovers, mainly about two, frequently four or more weeks after the bone marrow is engrafted, either by I.V. or direct injection into the bone marrow. By having the neoplastic tissue present in the bone marrow, one can determine the effect of the neoplastic cells on the proximal hematopoietic cells and by providing for other agents or organs, particularly thymus, establish the ability of the normal cells to respond to the presence of the neoplastic cells. In addition, one may investigate how the neoplastic cells displace or destroy the normal cells.

The various agents may be administered in a variety of ways. Depending upon the nature of the agent, one may use continuous infusion, employing various pumps which are available, which allow for long-term constant or varying infusion of a reagent. Alternatively, one may apply the drug parenterally, by administration intravascularly, intra-organ, intraperitoneally, subcutaneously, or the like. Each agent may be administered at varying concentrations to determine effective dosages, response to variation in dosage and the like. Dosages may vary from picograms to grams per kilogram of host. Other methods of administering the agent may be employed as appropriate.

Illustrative of various methods of using the bone marrow are the following. One can evaluate the efficacy of a wide variety of cytokines as to their effect on various cells in the bone marrow, the effect of compounds which have similar activities or are antagonistic to such cytokines. Depending upon the particular host, one can relate the activity observed in the host in comparison to the activity anticipated in a human. While the pharmacokinetics for the host may be different from the human, in many cases one can extrapolate between the host and the human, based on experience with other drugs having a similar chemical nature.

The use of cytokines may be divided into two possibilities: (1) a cytokine which is available from the stroma present in the bone and/or bone marrow; and (2) cytokines which are deficient in the bone and bone marrow. In the case of cytokines which are present in the bone marrow, one would first have to establish that the cytokines available in the bone marrow are inadequate, being below optimum concentration for cell proliferation and/or differentiation. Where the cytokine is substantially below optimum levels, then one can add the cytokine or its analogs and measure the effect on the hematopoietic cell population in the bone marrow. Where one wishes to study an antagonist, then if the stroma provides a sufficient amount of the cytokine, one can study the effect of the antagonist. Alternatively, if the stroma or bone marrow does not provide sufficient amount of the cytokine, the amount of cytokine can be augmented exogenously.

One can study the effect of radiation and agents on the effect of radiation. Thus, one can provide for irradiation substantially solely of the human bone marrow or of portions of the host or of the entire host. One can add various agents to the host to determine their ability to protect against radiation. Thus, one can determine the effect of agents as to their increasing or decreasing the effect of radiation on hematopoietic cells. One can compare the effect of the various agents on various levels of radiation, the effect of various levels of radiation on the different cell types, as well as the effect of the various agents as to the effect of radiation on the different cell types.

One can introduce various lymphomas or leukemias into the bone marrow, where the human lymphomas and leukemias will become established in the presence of bone marrow, which will be more of a natural setting for these cells than introducing these cells into xenogeneic hosts in the absence of normal human hematopoietic cells. In addition, one may provide for other organs, particularly a thymus, so that progenitors of T-cells may migrate from the bone marrow to the thymus and mature. One may then analyze the nature of the T-cells involved with the neoplastic tissue, determining the variable regions of the T-cell receptors, including the alpha, beta, gamma or delta chains as appropriate. In this manner, one may establish the nature of the variable regions of the T-cell receptors associated with the immune response to particular neoplastic cells. One may then expand these cells and use them therapeutically. If necessary, one may obtain autologous human stem cells from the host to be treated, introduce them into the bone marrow and tumor-containing immunocompromised host, allow them to mature to T-cells, and isolate these T-cells from the tumor. These T-cells may then be expanded and introduced into the patient from which they were derived for treatment of the neoplastic condition.

One may also study a wide variety of agents as to their effect on the tumor as well as on the normal hematopoietic cells in the bone marrow. Thus, one may develop a therapeutic index of the effect on the immune system as compared to the effect on the tumor. In this manner, drugs may be better evaluated as to their use in treating tumors while not having a seriously adverse effect on the immune system.

Drugs for the treatment of any other disease which drugs are introduced into the blood system may also be evaluated as to their effect on hematopoietic cells. Thus, one may administer a drug, maintain the dosage at a therapeutic level, and monitor the change in hematopoietic cells in the bone marrow or in the peripheral blood. Furthermore, by providing other lymphoid organs, such as thymus, spleen, lymph node, tonsil, and the like, one may also determine the effect of the drug on the population of hematopoietic cells in these various tissues.

One may also use the bone marrow for immunization, where a thymus and lymph node have been provided so that there is a population of T-cells present. In this manner, one may effectively evaluate vaccines for their ability to produce a strong immune response, where neutralizing antibodies are produced. The B-cell repertoire can be expanded by bone marrow implantation. One may evaluate various vaccines in relation to the MHC antigens of the particular bone marrow. The B-cells may be used for fusion with a myeloma cell line or for immortalization or other technique to produce immortalized cells or maintain B-cells in culture, which B-cells secrete specific antibodies to be used as monoclonal antibodies.

The host may be used for studying T and B lymphocyte interactions, in determining the manner of stimulation of T and B lymphocytes and the mechanism for the immune reaction. Individual lymphocytes may be cloned to evaluate their role in disease protection against disease. The bone marrow may find uses in determining the particular variable regions of the T-cell receptors associated with responses to particular pathogens, the effect of genetic diseases on the hematopoietic cell population, the effect of inactivation of a variety of genes on the hematopoietic cell population, and the like. The cells may be used in gene therapy, where the cells may be transformed, e.g., transfection, with genes which may provide for therapeutic effect, e.g., controlled release of insulin, adenosine deaminase and the like. Also, the cells may serve to study infectious diseases and the effect of agents on such diseases.

Of particular interest as an immunocompromised host is the mouse, more particularly the CB-17 scid/scid mouse. The mice of particular interest are those mice incapable of producing competent B- and/or T-cells. This will usually be as a result of lack of Class I and/or II major histocompatibility complex antigens, lack of stem cells, lack of recombinase, or another lesion. The mouse may be grafted with one or more bone slices of about 0.5 to 1.5, usually 1 cm. in length, the number of bone slices usually not exceeding five, more usually not exceeding two. As previously indicated, the bones will be transplanted subcutaneously or intraperitoneally. Desirably, the mice are preconditioned with 200–300, preferably about 250 rads of irradiation. It is noted that it usually takes from about three to four weeks after implantation for the bone marrow to recover from the grafting process, before hematopoiesis can be observed. Particularly, in the irradiated mice, relatively high levels of human circulating cells, particularly myeloid and lymphoid may be observed, generally being at least about 2% of the total number of peripheral blood cells, more usually at least 5%, and preferably 10% or higher. Usually, the percentage will not exceed about 60%, more usually not exceeding about 50%.

Other techniques for bone marrow ablation which may be employed by themselves or in combination with irradiation include cytotoxic drugs, immunotoxins, antibodies to lymphokines and growth factors, antibodies to natural killer cells, etc. The selection of cytotoxic drugs would be based on their ability to clear quickly from the lymphatic and blood circulatory systems, so as to rapidly be reduced to a non-cytotoxic level, prior to or shortly after the administration of the human bone marrow.

The following examples are offered by way of illustration and not by way of limitation.

EXPERIMENTAL

Example 1

Human fetal femurs and tibias (1–2 cm) at 17–22 gestational week (g.w.), which are known to be active in hematopoiesis, were cut along a longitudinal axis so that bone cortex as well as intramedullary regions could be exposed. These fragments were then surgically implanted subcutaneously into SCID mice. Homozygous CB-17 scid/scid mice were bred, treated with antibiotics as described (McCune et al., Science (1988) 241:1632), and used when 6–8 weeks old. Methoxyflurane anesthesia was applied during all operative procedures. Hematoxylin-eosin stained tissue sections were prepared from bone grafts 2 weeks and 8 weeks after implantation. The tissues were fixed in 20% formalin, decalcified with EDTA (1.7 mM) in HCl solution, paraffin embedded, and 4 μm sections were cut and stained with hematoxylin and eosin. Grafts were removed at varying intervals after implantation and analyzed for the presence of human hematopoietic activity.

The cell suspensions were prepared from implanted or normal bone marrow tissues, treated with 0.83% of ammonium chloride for 5–10 min at room temperature to lyse red blood cells, and washed with PBS. The cells were incubated with either biotinylated-MEM-43, biotinylated-Ly5.1, or biotinylated control antibodies for 45 min on ice, washed through a fetal bovine serum (FBS) cushion, and then stained with fluorescein conjugated (FITC-) avidin (Caltag Laboratories Inc.) for 45 min. Before flow cytometry, propidium iodide (PI) was added at final concentration of 10 μg/ml to gate out dead cells. Forward and side scattering patterns of the MEM-43 positive cells were obtained by four parameter flow cytometry using a single laser FACScan (Becton Dickinson Immunocytometry Systems).

Hematopoiesis in the grafts underwent an early crisis, followed by a recovery. At early stages of implantation (week 2–3), histological examination showed necrosis and/or fibrous changes in the marrow. No clear foci of hematopoietic cells could be found on histology sections, although bone elements including osteoblasts were well maintained. At 4–5 weeks, active hematopoiesis was observed at many sites within the engrafted bones. After 6–8 weeks, most of the grafts looked similar to normal human fetal bone marrow associated with lymphopoiesis, myelopoiesis, erythropoiesis, and megakaryocytopoiesis in a high degree of cellularity. The yield of the cells from the grafts 4–16 weeks after implantation were within the range of 5–50× $10^5$/grafts, which is approximately 10% of the input. Wright-Giemsa staining of these cells on cytospin preparations also exhibited the typical morphology of lymphoid, myeloid or erythroid cells at different maturational stages. These signs of active hematopoiesis were observed in more than 90% of the bone grafts and continued to 16 weeks after implantation.

The human origin of hematopoietic cells within the grafts was confirmed by flow cytometry with either MEM-43 (an antibody specific for a common antigen of human cells) or Ly5.1 (reactive with mouse pan-leukocyte antigen). In almost all the samples examined (57/60, between 2 and 12 weeks after implantation), more than 70% of the cells recovered from the grafts were stained with MEM-43 antibody, whereas only a small population (5–20%) of the cells were reactive with Ly5.1. The replacement of the human bone marrow with mouse hematopoietic cells was observed in some of the grafts incubated in vivo for over 20 weeks.

The characteristics of the hematopoietic cell populations in the bone marrow were analyzed by light scattering profiles using flow cytometry. Four distinctive clusters of hematopoietic cells, i.e., lymphoid (R1), blastoid (R2), myeloid (R3), and mature granulocyte (R4) populations were revealed in normal fetal bone marrow by forward and side scattering distributions (Table 1). Similar analyses with MEM-43 positive human cells recovered from the bone implants at various different time points after implantation were carried out. Cells recovered 2 weeks after implantation did not show clear cluster formation, indicating that these cells were of non-hematopoietic origin, while the human cells from grafts incubated longer than 4 weeks showed scattering profiles that were similar to those of normal fetal bone marrow cells. Thus, the kinetics of the appearance of human hematopoietic cells in the implanted bone detected by scatter analyses were found to be in accord with the histological observations as described above.

The cell surface phenotypes of the nucleated hematopoietic cells in the grafts were further analyzed with various antibodies specific for human lineage markers (Table 1). About 80% of the cells in the lymphoid (R1) region were B cells, positive for both CD10 and CD19. When stained for surface immunoglobulin, about 20% express IgM and about 4% express IgD as well. The ratio of cells with either κ or λ light chains was similar to that in normal bone marrow, suggesting that these B cells were not products of a monoclonal expansion. These findings strongly suggested that the differentiation of B-lineage cells was maintained as observed in the normal fetal bone marrow. A small number (<5%) of human T-lineage cells detected by CD7 antibody was found in this region. Approximately 60% of the cells in the myeloid (R3) region was found to express the CD15 antigen, specific for myelomonocytic cells, indicating that the major population of the cells in this region was the immature forms of myelomonocytic cells. Over 80% of the cells in the R4 region were also positive for this marker and the light scattering profile indicated that they were mature forms of granulocytes. The cell population in the blastoid (R2) region was a mixed population of $CD10^+19^+$ cells, $CD15^+$ cells, and cells lacking these markers. Furthermore, as observed in normal fetal bone marrow, a significant (5–10%) of cells in the R1 and R2 regions expressed CD34, a marker for bone marrow progenitor cells. Taken together, the cellular composition in each cluster in the implanted human bone marrow were found to be similar to those of normal fetal bone marrow. The proportion of these four regions within the nucleated hematopoietic cells in the grafted marrow was compared to that of normal fetal bone marrow. The percentage of mature granulocytes (R4 region) in total nucleated cells was found to be significantly lower in the grafts (12±7%) than in the normal fetal marrow samples (25±5%). In addition, the ratio between lymphoid and myeloid cells (R1/R3+R4) in the grafted marrow was significantly higher (approximately 2) compared to fresh marrow (approximately 1), indicating that either lymphopoiesis was promoted or myelopoiesis was suppressed in the grafted marrow.

cells and the total cell number recovered. Bone grafts from 5 different fetal donors (19–22 g.w.) were used for this experiment. CFU-GM and BFU-E were assayed by methylcellulose cultures, according to previously described methods (Skettino, et al., Blood (1988) 71:907). Briefly, the bone marrow cells were plated in 24 well plates at a concentration of 1–5×10$^4$/ml in 0.25 ml cultures containing 1% methylcellulose (1,500 centipoises, Sigma Chemical Co.) in Iscove's modified Dulbecco's medium (Gibco Laboratories) with 20% FBS, 0.05 mM 2-mercaptoethanol, 200 mM Lglutamine, 0.8% lept-albumin, 0.08% NaHCO3, and human recombinant erythropoietin (Amgen Biologicals) at the concentration of 2 u/ml, and 10% Mo conditioned media (Golde, et al., Blood (1978) 52:1068). The methyl-

TABLE 1

| Bone Marrow | Region (%) | % Positive ± Standard Deviation | | | | | | | | | |
|---|---|---|---|---|---|---|---|---|---|---|---|
| | | CD10 | CD19 | IgM | IgD | Igk | Igλ | CD15 | CD34 | MEM43 | Ly5.1 |
| Grafted | R1 (49 ± 11) | 82 ± 7 | 83 ± 7 | 20 ± 5 | 4 ± 2 | 7 ± 2 | 13 ± 3 | 1 ± 1 | 6 ± 3 | 86 ± 5 | 11 ± 5 |
| (n = 17) | R2 (25 ± 6) | 61 ± 10 | 66 ± 11 | 8 ± 6 | 3 ± 3 | 4 ± 3 | 6 ± 4 | 5 ± 3 | 9 ± 4 | 87 ± 12 | 9 ± 7 |
| | R3 (15 ± 8) | 7 ± 4) | 4 ± 2 | ND** | ND | ND | ND | 57 ± 16 | 2 ± 2 | 78 ± 17 | 9 ± 13 |
| | R4 (12 ± 7) | 13 ± 7 | 4 ± 2 | ND | ND | ND | ND | 83 ± 15 | <1 | 94 ± 5 | 4 ± 2 |
| Not Grafted | R1 (40 ± 9) | 76 ± 8 | 76 ± 6 | 19 ± 4 | 5 ± 1 | 6 ± 1 | 13 ± 2 | 1 ± 0 | 7 ± 1 | — | — |
| | R2 (18 ± 2) | 43 ± 7 | 48 ± 8 | 5 ± 3 | 3 ± 1 | 2 ± 1 | 2 ± 2 | 7 ± 4 | 16 ± 2 | — | — |
| (n = 7) | R3 (17 ± 4) | 8 ± 3 | 7 ± 3 | ND | ND | ND | ND | 80 ± 3 | 2 ± 2 | — | — |
| | R4 (25 ± 5) | 17 ± 10 | 3 ± 2 | ND | ND | ND | ND | 90 ± 9 | <1 | — | — |

**Not determined due to high non-specific staining.

The level of human erythropoietic activity was analyzed with antibodies specific for human glycophorin A (GPA). Flow cytometric analysis of human glycophorin A (GPA) expression in bone marrow cells from the grafts was performed. The cell suspensions were prepared from the grafts without ammonium chloride treatment. The cells were stained with biotinylated-anti-human GPA antibodies (a mixture of 6A7 and NN3 antibodies, which are specific for M-type or N-type of GPA, respectively (Bigbee et al., Mol. Immunol. (1983) 20:1353; Kyoizumi, et al., Cancer Res. (1989) 49:581), followed by FITC-avidin binding as described above. After final washing with PBS, the cells were fixed in 2.5% paraformaldehyde in PBS, and then incubated with PI at the final concentration of 1 µg/ml to stain nuclear DNA.

0.5–3% of nucleated cells (PI$^+$) from 4–12 week implants were found to express a high level of GPA. Expression of GPA was also detected in a small number of cells in the enucleated cell population (PI), indicating that final maturation to human erythrocytes was possible in the bone implants. Compared to the number of nucleated erythroid cells in normal fetal bone marrow (approximately 30% when counted on cytospin preparations), this population was small. A low level of erythropoiesis was also noticed on histology sections and on cytospin preparations. Thus, although the level of erythropoiesis was lower than normal, human erythroid precursors were able to differentiate into mature erythrocytes in the grafted bones.

The above results support the belief that human progenitor cells with self-renewal and multi-lineage capacity are functionally maintained when human bone grafts were implanted into SCID mice. To test this directly, kinetics of progenitor cell activities by colony forming assay in culture was examined.

The total number of colonies per graft was obtained by calculation based on the numbers of the colonies per 10$^5$ cellulose cultures were incubated at 37° C. in 7% CO$_2$ in air and were counted after 12 days to determine the number of colonies per well. CFU-C were characterized as having greater than 50 cells and consisted mainly of granulocytes and/or macrophages (CFU-GM) or multiple clusters of erythroid cells (BFU-E).

The number of granulocyte macrophage colony forming units (CFU-GM) and erythroid burst forming units (BFU-E) per 10$^5$ cells decreased to a low level at 2 weeks after implantation and increased by 4 weeks. Thereafter, the activities gradually decreased, and finally reached constant levels within the range of the activities of normal fetal bone marrow cells (approximately 100 CFU-GM and 200 BFU-E per 10$^5$ cells) for as long as 16 weeks after implantation. Almost all of the cells (>95%) recovered from the colonies were positively stained with MEM-43 antibody, but not with Ly5.1 antibody. Further, cells from CFU-GM and BFU-E colonies were demonstrated to express human lineage specific markers, CD15 or human GPA on the surface, respectively. Progenitor cell activity for the erythroid lineage was maintained in the bone grafts at a normal level even when, as described, erythropoiesis in the grafts was low.

The kinetics of progenitor cell activity and recovery after bone transplantation was shown in another fashion by plotting the total number of CFU per graft. The absolute number of both CFU-GM and BFU-E steeply increased (approximately 30-fold) from the samples at 2 weeks post-implantation to those at 4 weeks and reached plateau levels 6 weeks after implantation. Human progenitor cells for CFU-C proliferated rapidly between 2 to 4 weeks, and the bone marrow cell population appeared to enter a steady state after 6 weeks, maintaining constant levels of precursor activity in the grafts.

Finally, the presence of human cells in the peripheral circulation of SCID-hu mice with bone grafts was examined by FACS analysis, using the combination FITC-HLe1 antibody (the common human leukocyte antigen, CD45) and PE-W6/32 antibody (a monomorphic determinant of MHC-Class I). Human cells could be detected at significant frequency (0.1–3.0% of total lymphoid cells) in peripheral blood from more than half of the SCID-hu mice examined after 9 weeks of implantation. Most of the human cells in the peripheral blood expressed CD19 antigen, indicating that they are B-lineage cells.

To determine the effect of irradiation on human progenitors in the bone marrow, CB-17 scid/scid mice in which were implanted human fetal bone from various long bones 8 to 10 weeks before, were irradiated at various dose levels using a $^{137}Cs$ radiation source at a dose rate of 3.37 Gy/min. Immediately after irradiation, cells were recovered from implanted bones and the surviving fraction was assayed by CFU-C assay. The number of colonies were normalized per 10-cells and surviving fractions were calculated based on the number of colonies from a control mouse without irradiation as 100%.

marrow cells reported in McCulloch and Till, *Radiation Research* (1962) 16:822–832. Thus, the subject invention provides a novel demonstration of the ability of the subject animal model to evaluate the effect of radiation on human hematopoietic cells.

In the next study, the effect of erythropoietin was determined. The recombinant human erythropoietin was administered using an Alzet pump so as to provide for continuous infusion of the erythropoietin. The outcome is indicated in Table 3.

TABLE 2

In Vivo Effect of Irradiation on Human CFU-C

| Mouse | Donor | Dose | Bone | CFU-GM/ $10^5$ | Mean | SF* | BFU-E per $10^5$ | Mean | SF* | Total Colony per $10^5$ | Mean | SF* |
|---|---|---|---|---|---|---|---|---|---|---|---|---|
| 1729-1 | R008 20 gw | 0 Gy | Humerus | 117 | 131 | 1 | 144 | 147 | 1 | 261 | 279 | 1 |
| | | | Humerus | 144 | | | 152 | | | 296 | | |
| 1729-2 | | 0.5 Gy | Femur | 77 | 147 | 1.12 | 99 | 114 | 0.78 | 176 | 260 | 0.93 |
| | | | Femur | 216 | | | 128 | | | 344 | | |
| 1729-3 | | 1 Gy | Femur | 88 | 91 | 0.69 | 56 | 76 | 0.52 | 144 | 167 | 0.60 |
| | | | Femur | 131 | | | 96 | | | 227 | | |
| | | | Femur | 60 | | | 59 | | | 119 | | |
| | | | Femur | 85 | | | 93 | | | 178 | | |
| 1729-4 | | 2 Gy | Tibia | 19 | 22 | 0.17 | 11 | 16 | 0.11 | 30 | 38 | 0.14 |
| | | | Tibia | 24 | | | 21 | | | 45 | | |
| 1729-5 | | 4 Gy | Tibia | 4 | 5 | 0.038 | 0.3 | 1.2 | 0.008 | 4.3 | 6.2 | 0.022 |
| | | | Tibia | 6 | | | 2 | | | 8 | | |
| 1706-1 | K466 19 gw | 0 Gy | 2 Tibias | 480 | — | 1 | 536 | — | 1 | 1016 | — | 1 |
| 1706-2 | | 0.5 Gy | 2 Tibias | 303 | — | 0.63 | 320 | — | 0.60 | 623 | — | 0.61 |
| 1706-3 | | 1 Gy | 2 Humerus | 159 | — | 0.33 | 144 | — | 0.27 | 303 | — | 0.30 |
| 1706-4 | | 2 Gy | 2 Femurs | 25 | — | 0.052 | 17 | — | 0.032 | 42 | — | 0.041 |
| 1706-5 | | 4 Gy | 2 Femurs | 9 | — | 0.019 | 2 | — | 0.0037 | 11 | — | 0.011 |

*Surviving Fraction

When the survival fraction was plotted against the gamma ray dose in rads, it was found that the line was substantially similar to the line for gamma ray survival for mouse bone

TABLE 3

In Vivo Effect of Human Erythropoietin on Human Erythropoiesis Analyzed in the SCID-hu Mouse

| | | | | Human Erythropoiesis Erythroid/ | Mouse Erythropoiesis | |
|---|---|---|---|---|---|---|
| Mouse | Donor | Implants | EPO u/day* | Total Nucleated Cells + | RBC × $10^6/mm^3$ # | Hb gm/dl # |
| #1850-1 | K480A-20 wk | Femur (MFP) | 20 | 17.9% | 11.41 | 17.7 |
| #1850-2 | | Femur (MFP) | — | 3.4 | 9.04 | 14.3 |
| #1850-3 | | 2 Tibias (MFP) | 1 | 7.0 | 9.53 | 15.5 |

TABLE 3-continued

In Vivo Effect of Human Erythropoietin on Human Erythropoiesis Analyzed in the SCID-hu Mouse

| Mouse | Donor | Implants | EPO u/day* | Human Erythropoiesis Erythroid/ Total Nucleated Cells + | Mouse Erythropoiesis RBC × $10^6/mm^3$ # | Hb gm/dl # |
|---|---|---|---|---|---|---|
| #1850-4 | | 2 Tibias (MFP) | 20 | 28.5 | 10.14 | 16.5 |
| #1850-5 | | 2 Tibias (MFP) | — | 5.6 | 9.75 | 16.0 |
| #1890-1 | K486-19.5 wk | Femur (MFP) | — | 8.1 | 8.94 | 15.1 |
| #1890-2 | | Femur (MFP) | 1 | 7.5 | 9.32 | 15.7 |
| #1890-3 | | Femur (MFP) | 20 | 20.6 | Not Done | 19.5 |
| #1890-4 | | Femur (MFP) | — | 2.7 | 8.87 | 14.1 |
| #1890-5 | | Femur (MFP) | 20 | 19.5 | 11.78 | 18.1 |

*Recombinant human EPO was administered through Alzet 2001 pump.
+ Percentage of erythroid cells in human bone marrow analyzed on Wright-Giemsa stained cells.
Mouse peripheral blood was analyzed by cell counter (Serono Baker Diagnostics).

The results show that one can use the bone marrow to determine the activity of a factor in hematopoiesis, in this instance erythropoiesis, or to evaluate other agents which may be agonists, antagonists or enhancing agents. Also, one can see the effect of the factor on the total number of cells, so that one can monitor not only proliferation of cells in a particular compartment, but the total number of cells, in the bone marrow, peripheral blood, or both.

Simple surgical implantation of the human fetal bone fragments into SCID mice results in active human hematopoiesis. Cells of multiple lineages, in different maturational stages, were maintained inside the grafts. Except for low erythropoietic activity, the subpopulations of hematopoietic cells in the grafts were demonstrated to be very similar to those found in the normal fetal bone marrow. Human progenitor cell activities for multiple lineages were also demonstrated in the CFU-C assay. All of these hematopoietic activities were maintained in vivo for at least as long as 16 weeks after implantation. A suitable microenvironment for the maintenance of human progenitor cells and for induction of their differentiation were successfully introduced into a mouse has been shown. The kinetic studies of the progenitor cell activity in the grafts demonstrate that there are regulatory mechanisms which promote rapid recovery of hematopoiesis in damaged bone marrow and permit maintenance of a steady state thereafter.

Example 2

Bone pieces were transplanted into either untreated mice (6–10 weeks old) or mice (6–10 weeks old) pretreated with radiation from a cesium 137 source. The mice are treated with either whole body irradiation or irradiation of the long bones. Mice treated with whole body irradiation receive 200 to 400 rads on a single dose. Alternatively, the mice are treated with 600 rads after shielding of the thorax and abdomen with a lead shield. The mice are anesthetized with Nembutol prior to shielded irradiation. The mice were CB-17.5 scid/scid mice. In addition, some of the mice were treated with exogenous human IL-3 in two 1 μg doses per day. The fetal bone pieces are prepared from fetuses of 18–22 week gestation by first removing all of the soft tissues and cartilagenous portions from the bone. The bones are then cross sectioned at 2–5 mm intervals. The mice are prepared by injection ip of Nembutol. Once the mice are fully anesthetized, a 1 cm incision is made in the skin as well as the underlying peritoneum. The bone fragments are then placed into the peritoneal cavity randomly. Approximately 25 mm to 1.5 cm of a femur, tibia or humerus is implanted into each mouse. The mice which are irradiated are irradiated within 24 hours of the subsequent implantation of the fetal bone.

After two to six weeks, the percentage of human cells in the peripheral blood is determined by employing monoclonal antibodies specific for human hematopoietic cell markers. In un-irradiated mice a low level of human cells is observed in the peripheral blood by FACScan. The positive cells vary from about 0–1.6 percent. Furthermore, injection of IL-3 does not significantly affect the percentage of positive cells. In contrast, the mice irradiated before marrow transplantation showed between 1.5 and 30 percent human cells in the peripheral blood. These cells appear to be of the nyelomonocytic lineage. They show no staining with T or B cell markers (CD 3, 4, 8, 19), although they do stain for the myeloid cell marker (CD33). Furthermore, the human cells have a high side scatter profile indicating that they are of the myelomonocytic lineage. In addition, two of the four mice which were irradiated before implantation show low but significant levels of serum immunoglobulin after six weeks.

One can obtain high levels of human cells in an immunocompromised mouse at least partially ablated of endogenous bone marrow, by implanting relatively large amounts of human bone marrow, particularly with the stromal bone tissue. The human bone marrow implanted after irradiation provides a mouse which results in substantial numbers of cells of human myelomonocytic lineage and can provide for cells of other lineages as well, such as lymphoid.

This subject chimeric system provides a small animal model for the analysis of human hematopoiesis and its disease states. After engraftment, the human bone marrow can be manipulated in a systematic way. The consequences of such manipulations can be read out by various methods, as described. In vivo assay systems to read out human stem cell activity, equivalent to the mouse CFU-S assay are now available. Hematopoietic cells derived from diseased marrow, e.g., as in leukemias or genetic disorders, may be introduced into previously implanted allogeneic fetal bone grafts to study malignancy and the effects of growth factors and/or drugs which might modulate normal hematopoiesis or disease states. For human gene therapy trials, this model can also serve as a valuable system to test the long-term expression of exogenous genes introduced into human hematopoietic cells.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A chimeric immunocompromised mouse, said mouse comprising:
   an immunodeficient mouse host lacking functional syngeneic lymphocytes as a result of a genetic defect in immunoglobulin and T cell receptor gene rearrangement; and
   vascularized normal human fetal bone marrow and human fetal stroma resulting from the implantation of a human fetal bone or fragment thereof grown in said immunodeficient mouse host for a period of at least four weeks.

2. A chimeric immunocompromised mouse according to claim 1, wherein said immunocompromised mouse further comprises an exogenous agent which modulates hematopoiesis.

3. A chimeric immunocompromised mouse according to claim 2, wherein said exogenous agent is a drug.

4. A chimeric immunocompromised mouse according to claim 1, wherein said chimeric immunocompromised mouse further comprises at least one other human lymphoid organ.

5. A chimeric immunocompromised mouse, said mouse comprising:
   a scid/scid mouse host; and
   vascularized normal human fetal bone marrow and human fetal stroma resulting from the implantation of a human fetal bone or fragment thereof grown in said scid/scid mouse host for a period of at least four weeks.

6. A chimeric immunocompromised mouse according to claim 1, wherein said human fetal bone marrow further comprises lymphomas or leukemias introduced during or after bone marrow recovery.

7. A method of determining the effect of an agent on hematopoiesis of human fetal bone marrow, said method comprising:
   subjecting a chimeric mouse according to claim 1 to said agent; and
   determining the effect of said agent on hematopoiesis by measuring at least one cell type in said bone marrow or in the peripheral blood of said mouse.

8. A method according to claim 7, wherein said agent is radiation.

9. A method according to claim 7, wherein said agent is a cytokine.

10. A method according to claim 9, wherein said cytokine is erythropoietin.

11. A chimeric immunocompromised mouse according to claim 5, wherein said human fetal bone or fragment thereof is cut along a longtitudinal axis.

12. A chimeric immunocompromised mouse according to claim 11, wherein said immunocompromised mouse further comprises an exogenous agent which modulates hematopoiesis.

13. A chimeric immunocompromised mouse according to claim 12, wherein said exogenous agent is a drug.

14. A chimeric immunocompromised mouse according to claim 11, wherein said chimeric immunocompromised mouse further comprises at least one other human lymphoid organ.

15. A chimeric immunocompromised mouse according to claim 11, wherein said mouse is a C.B-17 scid/scid mouse.

16. A chimeric mouse according to claim 11, wherein said human fetal bone or fragment thereof is implanted subcutaneously.

17. A method of determining the effect of an agent on human hematopoiesis, said method comprising:
   subjecting a chimeric mouse according to claim 5 to said agent; and
   determining the effect of said agent on hematopoiesis by measuring at least one cell type in said bone marrow or in the peripheral blood of said mouse.

18. A method according to claim 17, wherein said agent is radiation.

19. A method according to claim 17, wherein said agent is a cytokine.

20. A method according to claim 19, wherein said cytokine is erythropoietin.

* * * * *